United States Patent
Blank et al.

(10) Patent No.: US 6,888,920 B2
(45) Date of Patent: May 3, 2005

(54) LOW-COST, HIGH PRECISION GONIOMETRIC STAGE FOR X-RAY DIFFRACTOGRAPHY

(76) Inventors: Basil Eric Blank, 1255 Hinging Post Rd., Ithaca, NY (US) 14850; Alexander Khosro Deyhim, 320 Blackstone Ave., Ithaca, NY (US) 14850

(*) Notice: Subject to any disclaimer, the term of this patent is extended or adjusted under 35 U.S.C. 154(b) by 242 days.

(21) Appl. No.: 10/234,431

(22) Filed: Sep. 3, 2002

(65) Prior Publication Data

US 2004/0042584 A1 Mar. 4, 2004

(51) Int. Cl.[7] .......................... H05G 1/00; G01N 23/20; G02B 7/00
(52) U.S. Cl. .......................... 378/81; 378/79; 378/208; 358/811; 358/819; 358/822
(58) Field of Search .............. 378/79, 80, 81, 378/208; 359/811, 819, 822

(56) References Cited

U.S. PATENT DOCUMENTS

| | | | |
|---|---|---|---|
| 3,564,240 A | * 2/1971 | Thomas, Jr. | 378/81 |
| 4,088,396 A | 5/1978 | Edelstein | 350/252 |
| 4,759,130 A | 7/1988 | Goldowsky | 33/1 |
| 4,938,564 A | 7/1990 | Romero | 350/252 |
| 4,972,448 A | 11/1990 | Munekawa | 378/81 |
| 5,138,496 A | 8/1992 | Pong | 359/822 |
| 5,475,728 A | 12/1995 | Smith et al. | 378/81 |
| 5,502,598 A | 3/1996 | Kimura et al. | 359/814 |
| 5,561,912 A | 10/1996 | Strange | 33/573 |
| 5,640,437 A | 6/1997 | Grueninger | 378/81 |
| 6,198,580 B1 | 3/2001 | Dallakian | 359/822 |
| 6,285,736 B1 | * 9/2001 | Dosho | 378/79 |
| 6,388,262 B1 | 5/2002 | Alani et al. | 250/442.11 |

* cited by examiner

Primary Examiner—David V. Bruce
Assistant Examiner—Allen C. Ho
(74) Attorney, Agent, or Firm—Anne M. Schneiderman

(57) ABSTRACT

A low-cost, high precision goniometric stage, for use in x-ray diffractography or in optical systems, with a spherical sector supported on at least one bearing, a top surface of the spherical sector that is used for mounting an object, a center of rotation located within the object, a rod or other member that is disposed below the spherical bearing surface, preferably orthogonal to the rotational axes, stepper motors or other actuators to move the device and a mechanical linkage between the rod and the motors.

20 Claims, 2 Drawing Sheets

LOW-COST, HIGH PRECISION GONIOMETRIC STAGE FOR X-RAY DIFFRACTOGRAPHY

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of motion systems and more specifically to a low-cost, high precision goniometric stage for use in x-ray diffracto-graphy or optical systems. Goniometers have been used for many years to measure angular relationships begriming with Wollaston's goniometer (1807) for measuring the angle between crystal faces. Recently single-tilt and double-tilt sample holders have been widely used in electron microscopy and in x-ray diffractometers. In most applications the goniometer rotates a sample around two axes and is often coupled with rotational and translational stages to provide up to six degrees of freedom.

As x-ray diffractography has advanced the need for precise sample positioning has become more stringent. Analyzer crystals, zone plates, polarization analyzers, quarter-wave plates and small mirrors must be rotated to micro- and nano-radian accuracy. Stability and repeatability have also become increasingly important as analysis times can require several hours or more.

Various techniques are currently used to solve this positioning problem. Most schemes rely upon specialty mechanisms such as stacks of circles, arc-segments or goniometric cradles machined to different radii that produce axes with orthogonal rotations about a point. Such devices are commercially available from, for example, Huber Diffraktionstechnik GmbH. There are usually substantial stages and fixtures mounted on these positioners to accommodate large crystals, water cooling mounts or fast response piezo-driven stages. Other approaches to positioning have been proposed but not widely adopted.

Goldowsky, U.S. Pat. No. 4,759,130 (1988) developed a goniometer head with a resolution of 0.001°. Displacements were applied to a cantilevered rod in such a way that its free end was not displaced but could be rotated about two orthogonal axes. Neither the resolution nor the size of the stage are, however, satisfactory.

Gimbal mounts allow two axes of rotation and have been used in many applications. Gimbals mounts were used by Alani et al, U.S. Pat. No. 6,388,262 (2002) in an application for transmission electron microscopes. No resolution was stated, however, gimbal mounts with a resolution of less than 1 arc-sec are widely available.

"Optical mount with independently orthogonally adjustable element", U.S. Pat. No. 4,088,396—Edelstein (1978) teaches the use of an optical mount which employs a spherical bearing surface. This is properly termed a kinematic device since the axes of rotation are located behind the optical component. Several subsequent patents use the spherical bearing but move the rotational axes to intersect on the optical component's surface. These include: Romero in "Gimbal Assembly", (U.S. Pat. No. 4,938,564—1990); Pong in "Adjusting Mechanism for a lens", (U.S. Pat. No. 5,138,496—1992)and Kimura et al in "Lens frame supporting mechanism" (U.S. Pat. No. 5,502,598—1996). They differ in the method of adjustment. A patent by Dallakian, U.S. Pat. No. 6,198,580 (2001), also uses a spherical bearing but achieves superior resolution with his adjusting means by providing a means to bias the bearing. A commercially available version of this design, available from Newport Corp., has a resolution of 0.3 arc sec when differential micrometers are used for adjustment.

A goniometer stage for use in x-ray diffractography is taught in U.S. Pat. No. 5,475,728 "Eucentric motion system", Smith et al (1995). It consists of a triangular plate, with a sample stage at the center, supported on three vertical actuators. In one embodiment a spherical bearing is mounted underneath the stage and biased with springs. The spherical bearing prevents in-plane movement of the stage, however, it is located on a sliding shaft that allows vertical movement making this a kinematic type mount. As a consequence all three actuators must be controlled in order to maintain a constant sample height. Significantly, the spherical bearing is designed to have its center of rotation above the stage.

Existing designs for goniometers are unnecessarily large, complex and costly. All of the devices described employ means of adjustment that project beyond the area that may be used for sample mounting. Excepting Smith et al all of the devices that utilize a spherical bearing surface rely on direct surface to surface contact which, due to static frictional forces, reduces their precision.

Gimbal type mounts and those optical mounts with spherical bearings are not suitable since the axes of rotation are below the sample. This necessitates simultaneous in-plane and vertical adjustments when used for x-ray diffractography and introduces additional positioning error.

The eucentric motion system of Smith et al correctly locates the axes of rotation above the sample stage and utilizes a spherical bearing surface supported on ball-bearings to constrain certain motions. It is still, however, unnecessarily large and complex and requires vertical correction.

BRIEF SUMMARY OF THE INVENTION

The primary object of the invention is to allow independent rotations of an object, when mounted on a stage, around two intersecting axes.

Another object of the invention is to rotate an object with an angular resolution and repeatability that is superior to existing devices.

Another object of the invention is to rotate objects about a point within the object.

A further object of the invention is to have the capacity to support high loads.

Yet another object of the invention is to reduce the mass of the stage and thereby increase the speed of response.

Still yet another object of the invention is to reduce the size of the stage.

Another object of the invention is to lower the cost of the stage.

Another object of the invention is to simplify maintenance and increase the reliability of the stage.

A further object of the invention is to easily scale the device for larger loads, greater accuracy, faster response, etc.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a low-cost, high precision goniometric stage for x-ray diffractography, or for use in optical systems, comprising: a spherical sector supported on at least one bearing, a top surface of said spherical sector that is used for mounting a sample or device, a center of rotation located above said top surface, a rod or other member that is disposed below the spherical bearing surface, preferably orthogonal to the rotational axes, stepper motors or other means to move the device and a mechanical linkage between the rod and the means to move the device.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

In order to ease understanding the various drawings use like reference members to represent like parts of the invention.

Figure 1:
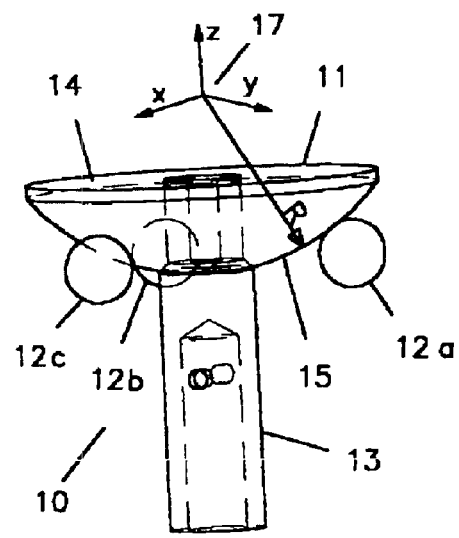
FIG. 1 is a perspective view of the goniometer stage, spherical bearing surface and support bearings.

In accordance with the present invention FIG. 1 shows a preferred embodiment of the goniometer bearing assembly 10 for use in x-ray diffractography. Directions x, y, and z, used in the description, are indicated by the right-hand, orthogonal triad 17 which is located at the center of rotation of the bearing assembly 10. A spherical sector 11, made from a hardened steel or other material, preferably with a hardness of at least 20 Rockwell C, has an flat, upper surface 14, which serves as the stage, and a spherical bearing surface 15. Spherical sector 11 may be machined using EDM from, for example, a 3-inch diameter AISI type 52100 steel ball, available from McMaster-Carr Supply Co. Other materials that could be used include, but are not limited to, high-carbon steels, 400-series stainless steels, ceramics, Invar, or titanium and its alloys.

The bearing surface 15 is preferably supported on at least three hardened steel ball bearings 12a, 12b and 12c such as are widely available. Preferred materials are identical to those listed for the spherical sector 11. These at least three ball bearings 12a–12c and the radius R of spherical bearing surface 15 define the center of rotation which lies on the axis of symmetry of the bearings 12a–12c. A rod 13 or other connecting means is attached to spherical sector 11 for the purpose of rotating said sector about the x and y-axes. Said rod 13 is attached by, for example, a threaded hole in spherical sector 11. It is preferred that the longitudinal axis of rod 13 is normal to, and passes through the center of, stage 14.

Figure 2:
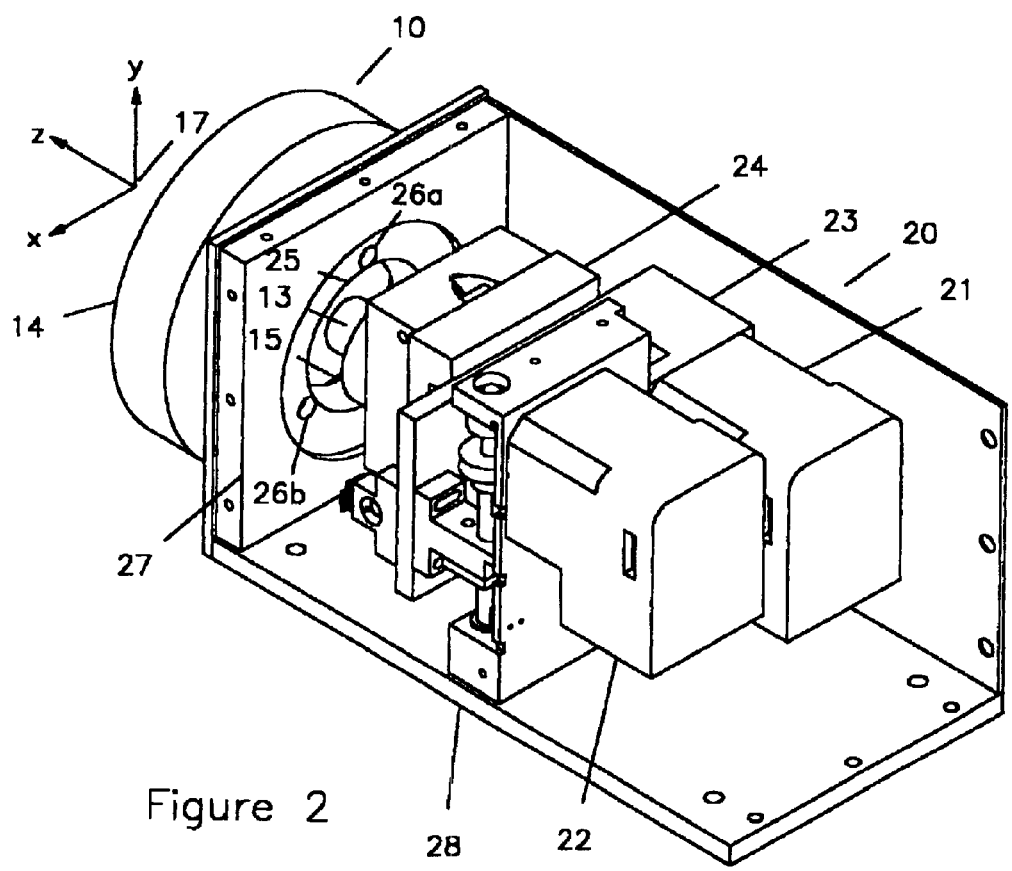
FIG. 2 is an isometric view of the goniometer including drive mechanism.

FIG. 2 shows the goniometer bearing assembly 10 with its associated drive mechanism 20. Once again a right-hand, orthogonal triad 17 that is located at the center of rotation of the bearing assembly 10 is shown to aid in the discussion. End plate 27 of the drive mechanism 20 is provided with a large hole 25 and three smaller, countersunk holes 26a–26c (only two of these latter are visible in the figure). Rod 13 projects through hole 25 where it engages with stage 24 via a mechanism shown in FIG. 3.

Figure 3:
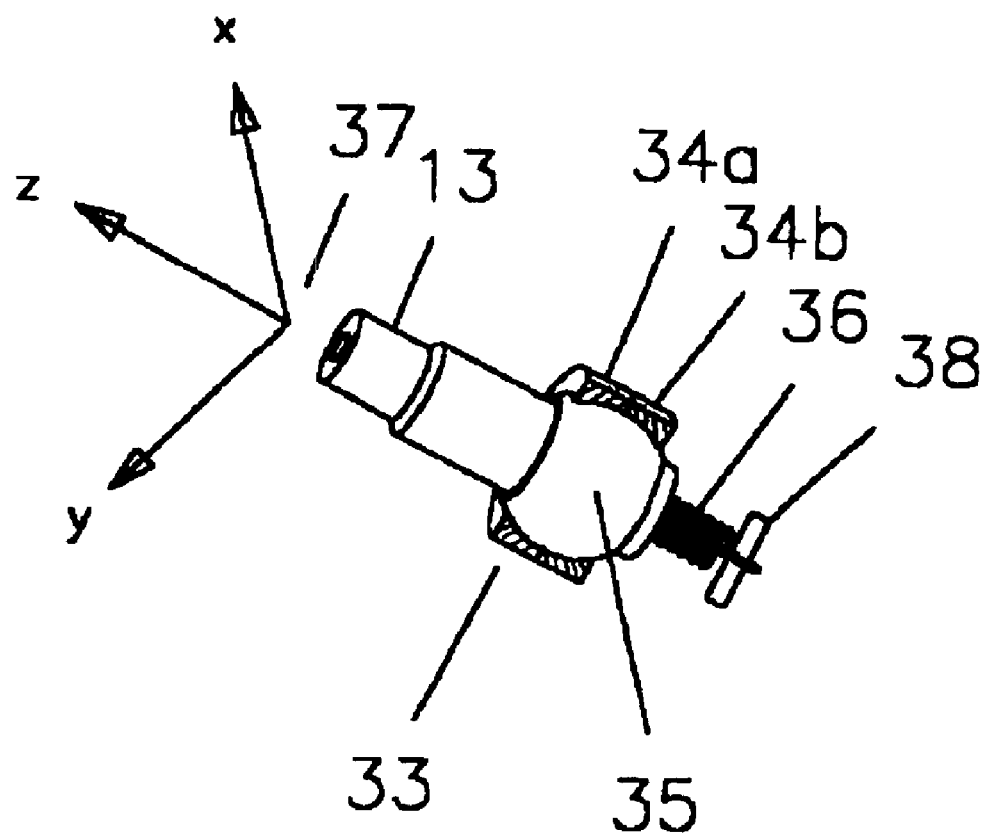
FIG. 3 is an isometric view of the linkage between the goniometric stage and the drive mechanism.

Referring now to FIG. 3 rod 13 is shown with a spherical bearing 33 comprising ball 35 and upper and lower sockets 34a and 34b, respectively. Said ball and sockets may be made from a wide range of materials, may have anti-friction coatings or be made from low friction materials, such as PTFE. Such bearings are widely available for example from McMaster-Carr Supply Co. Ball 35 has been provided with a through-hole so that rod 13 may slide freely through it. Spring 36 is provided to apply a force along the longitudinal axis of rod 13. Spring 36 is retained at its other end by a pin 38 or other well known means. Spherical bearing 33 and pin 38 are retained in stage 24 (not shown) by, for example, press-fitting into place. Said bearing, spring and pin transmit the translation of drive mechanism 20 to the rotation of the goniometer bearing assembly 10 (both shown in FIG. 2). Translation of bearing assembly 33, in the x- and y-directions defined by triad 37, produces both a translation and a rotation of rod 13 relative to the bearing 33. Ball 35 must, therefore, rotate within the upper and lower sockets 34a and 34b and slide along rod 13.

Referring once again to FIG. 2 it will be understood that spring 36 (not shown) applies a load along the longitudinal axis of rod 13, forcing bearing surface 15 against the three bearings 12a–12c (not visible). This force also maintains said three bearings in the countersunk holes 26a–26c.

The means for translating stage 24 is now described. Stepper motor drive 22 is mounted on base plate 28 which is rigidly connected to end plate 27. Motor drive 22 moves stage 23, on which motor drive 21 and stage 24 are mounted, in the y-direction through a series of gears (not indicated). Motor drive 21 is mounted such that it may independently move stage 24 in the x-direction through a second series of gears (not shown). Such gear trains are commercially available and are well known to those versed in the art and are, therefore, not described in detail. Translation of stage 24 in the x- and y-directions indicated by triad 17 imparts rotation of the stage surface 14 about these two axes in the manner heretofore described.

It will be understood by those well versed in the art that changes in the length of rod 13, the radius of the spherical surface 15 and the gearing of the movement means 20 can be made in order to improve positioning accuracy, response speed, load carrying capacity etc.

All of the parts and mechanisms described above are widely available and are used for many purposes. The elimination of specially built devices ensures that the objective of low cost is met. Testing has proven that the invention also meets the objective of high precision—the design heretofore described has achieved rotational resolution of 0.0144 arc-sec with a repeatability of 3.6e-5 arc-sec and a load capacity of 11.3 kgf.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A low-cost, high precision goniometric stage for x-ray diffractography comprising:
   a spherical sector supported on at least one spherical bearing surface;
   a flat upper surface of said spherical sector that is used for mounting a sample or device;
   two intersecting axes of rotation disposed within the sample or the device;
   a connecting member that is attached to said at least one spherical bearing surface;
   movement means to move the connecting member; and
   a mechanical linkage between the connecting member and the movement means.

2. The goniometric stage as set forth in claim 1 wherein said linkage converts translations of said movement means to rotations of said upper surface.

3. The goniometric stage as set forth in claim 2 wherein said linkage comprises a spherical bearing with a connecting member slidably mounated within said bearing, said connecting member being connected to said upper surface.

4. The goniometric stage as set forth in claim 1 wherin said spherical sector is held against said at least one bearing surface by at least one spring.

5. The goniometric stage as set forth in claim 1 wherein said spherical sector is supported on at least three ball bearings.

6. The goniometric stage as set forth in claim 5 wherein said spherical sector is held against said at least three ball bearings by at least one spring.

7. The goniometric stage as set forth in claim 5 wherein more preferably exactly three ball bearings support said spherical sector.

8. The goniometric stage as set forth in claim 7 wherein said spherical sector is held against said exactly three ball bearings by at least one spring.

9. The goniometric stage as set forth in claim 1 wherein said means to move the connecting member comprises at least two motors.

10. The goniometric stage as set forth in claim 1 wherein said connecting member is preferably orthogonal to said rotational axes.

11. A low-cost, high precision positioning stage for use with optical systems comprising:
    a spherical sector supported on at least one spherical bearing surface;
    a flat upper surface of said spherical sector that is used for mounting a sample or device;
    two intersecting axes of rotation disposed within the sample or the device;
    a connecting member that is attached to said at least one spherical bearing surface;
    movement means to move the connecting member; and
    a mechanical linkage between the connecting member and the movement means.

12. The positioning stage as set forth in claim 11 wherein said linkage converts translations of said movement means to rotations of said upper surface.

13. The positioning stage as set forth in claim 12 wherein said linkage comprises a spherical bearing with a connecting member slidably mounted within said bearing, said connecting member being connected to said upper surface.

14. The positioning stage as set forth in claim 11 wherein said spherical sector is held against said at least one bearing surface by at least one spring.

15. The positioning stage as set forth in claim 11 wherein said spherical sector is supported on at least three bail bearings.

16. The positioning stage as set forth in claim 15 wherein said spherical sector is held against said at least three ball bearings by at least one spring.

17. The positioning stage as set forth in claim 15 wherein more preferably exactly three ball bearings support said spherical sector.

18. The positioning stage as set forth in claim 17 wherein said spherical sector is held against said exactly three ball bearings by at least one spring.

19. The positioning stage as set forth in claim 11 wherein said means to move the connecting member comprises at least two motors.

20. The positioning stage as set forth in claim 11 wherein said connecting member is preferably orthogonal to said rotational axes.

* * * * *